(12) United States Patent
Stephens

(10) Patent No.: US 7,678,083 B2
(45) Date of Patent: Mar. 16, 2010

(54) PRE-CURVED CATHETER TIP

(75) Inventor: John Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 0 days.

(21) Appl. No.: 11/210,549

(22) Filed: Aug. 23, 2005

(65) Prior Publication Data

US 2006/0047268 A1 Mar. 2, 2006

Related U.S. Application Data

(60) Provisional application No. 60/604,228, filed on Aug. 25, 2004.

(51) Int. Cl.
| | |
|---|---|
| *A61M 5/32* | (2006.01) |
| *A61B 17/06* | (2006.01) |
| *A61B 19/02* | (2006.01) |
| *A61C 15/00* | (2006.01) |
| *B65D 83/10* | (2006.01) |

(52) U.S. Cl. .................. 604/174; 206/438; 206/364
(58) Field of Classification Search ............. 604/533, 604/43, 174, 178, 179, 180, 264, 523; 206/364, 206/438, 363, 365, 366
See application file for complete search history.

(56) References Cited

U.S. PATENT DOCUMENTS

| | | | |
|---|---|---|---|
| 4,435,174 A | | 3/1984 | Redmond et al. |
| 4,453,933 A | | 6/1984 | Speaker |
| 5,848,691 A | * | 12/1998 | Morris et al. ............... 206/364 |
| 5,916,199 A | | 6/1999 | Miles |
| 5,947,284 A | * | 9/1999 | Foster ......................... 206/364 |
| 5,947,931 A | | 9/1999 | Bierman |
| 6,001,081 A | * | 12/1999 | Collen ......................... 604/174 |
| 6,719,135 B2 | * | 4/2004 | Armijo ........................ 206/364 |

(Continued)

FOREIGN PATENT DOCUMENTS

WO    WO 99/56802    * 11/1999

OTHER PUBLICATIONS

Medcomp Product Drawing, "Tray drawing with Catheter Product"; Medical Components, Inc., Harleysville, PA (Jan. 2005).

(Continued)

*Primary Examiner*—Matthew F DeSanto
(74) *Attorney, Agent, or Firm*—Anton P. Ness; Fox Rothschild LLP

(57) ABSTRACT

A catheter retaining clip (100) including first and second generally straight body portions (104,106), each of which extends along a longitudinal axis parallel to the other and includes a retention section. The generally straight body portions are connected by an extension piece (116 or 240) that extends generally from one generally straight body portion to the other generally straight body portion. The extension piece (116) may extend around a 180° curve that defines the curve of the catheter to be inserted into the clip, and a U-shaped channel (120) extends through the first and second generally straight body portions and the extension piece; the clip is installed onto a catheter (50) so that the catheter lies in the U-shaped channel and is retained therein by two or three retention sections or locking clasps (130). The present invention also provides methods of installing a catheter within the clip and methods of removing a catheter from within the clip.

20 Claims, 6 Drawing Sheets

U.S. PATENT DOCUMENTS

2002/0120224 A1    8/2002    Zia et al.
2002/0130059 A1    9/2002    Armijo

OTHER PUBLICATIONS

International Search Report, PCT/US05/30062, dated May 15, 2006 (3 pages).

Written Opinion, PCT/US05/30062, dated May 15, 2006, (3 pages).

Medcomp Catalog, "HEMO-CATH ® Silicone Catheters", p. 10 (Apr. 2003) (3 pages).

Medcomp Drawing No. 3912, "Clip, HEMOCATH Extension Lines", one sheet (Oct. 15, 1997).

Preliminary Report on Patentability, PCT/US05/30062 dated Nov. 2, 2006 (4 pages).

* cited by examiner

PRE-CURVED CATHETER TIP

CROSS-REFERENCE TO RELATED APPLICATION

The present application claims priority from Provisional patent application Ser. No. 60/604,228 filed Aug. 25, 2004.

FIELD OF THE INVENTION

This invention relates to medical devices and more specifically to pre-curved catheters and the use of a device to properly maintain the shape of a pre-curved catheter and to protect the catheter from damage during sterilization and packaging.

BACKGROUND OF THE INVENTION

In the manufacture of certain catheters, it is desirable to provide a curved shape thereto between the proximal and distal ends. When a stylet is installed into such a catheter assembly during manufacture to later assist in the insertion of the catheter into a patient, the stylet is sufficiently stiff that it tends to try to straighten the curvature of the catheter assembly that is desired. Therefore, it is desired to provide for maintaining the curvature of the catheter assembly during sterilization, packaging and shipping.

SUMMARY OF THE INVENTION

The present invention is a removable clip for being secured to a catheter assembly at the curvature of the catheter, to maintain the curvature thereof during sterilization, packaging and shipping until it is removed therefrom immediately prior to insertion of the catheter assembly into a patient. The clip includes first and second generally straight portions that are spaced apart and generally coextend parallel to each other, joined together by an extension piece. At least the first and second generally straight portions have retention sections such as locking clasps above U-shaped channels therethrough into which the catheter is insertable and securable, with the curved portion of the catheter isolated on one side of the clip while the remainder of the distal and proximal catheter portions are on the opposite side of the clip.

In one embodiment of the present invention, the extension portion extends around a curve that defines the desired curve of the catheter to be maintained, in which case the U-shaped channel extends continuously from the first generally straight portion through the extension to the second generally straight portion, and the extension piece may include an additional locking clasp. In another embodiment, the extension piece extends directly between the first and second generally straight portions, and the catheter is not disposed along the extension piece.

The methods of the present invention for installing the catheter into the clip comprise: forcing respective catheter lumen portions past respective retention sections at least on the first and second generally straight portions of the clip until the catheter lumen portions are secured to the clip. The methods for catheter removal comprise either: forcing the catheter lumens past the retention sections in a common direction away from the clip; or, pulling the catheter through the U-shaped channel of the clip until the distal end passes therethrough and outwardly from the second generally straight portion.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
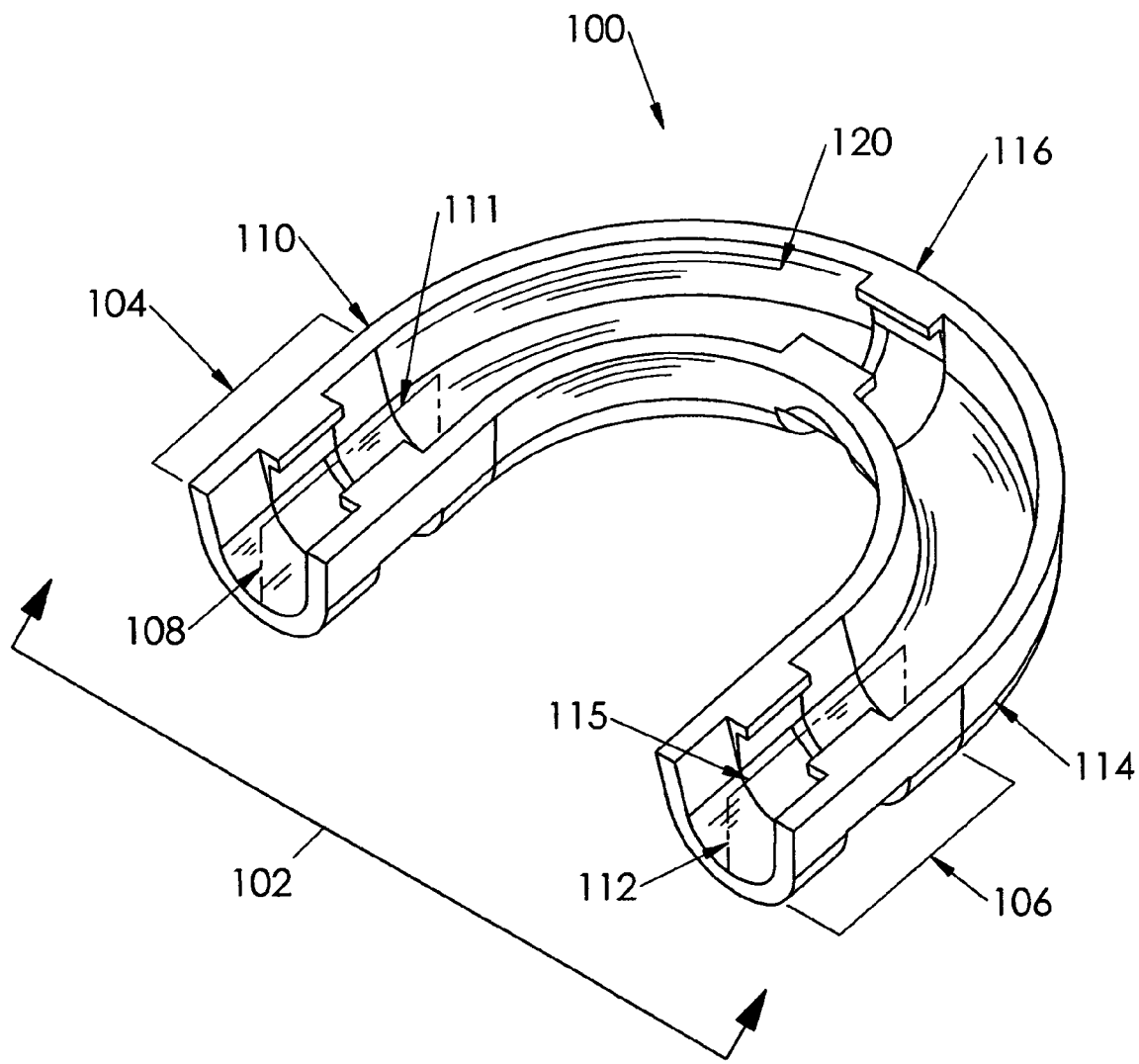
FIG. 1 is a perspective view of a pre-curved catheter clip according to a first preferred embodiment of the present invention.

In the drawings, like numerals indicate like elements throughout. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention. As used herein, the word "distal" is defined as being close to the insertion end of a catheter, and the word "proximal" is defined as being close to the end of the catheter that generally remains outside of the body.

Figure 2:
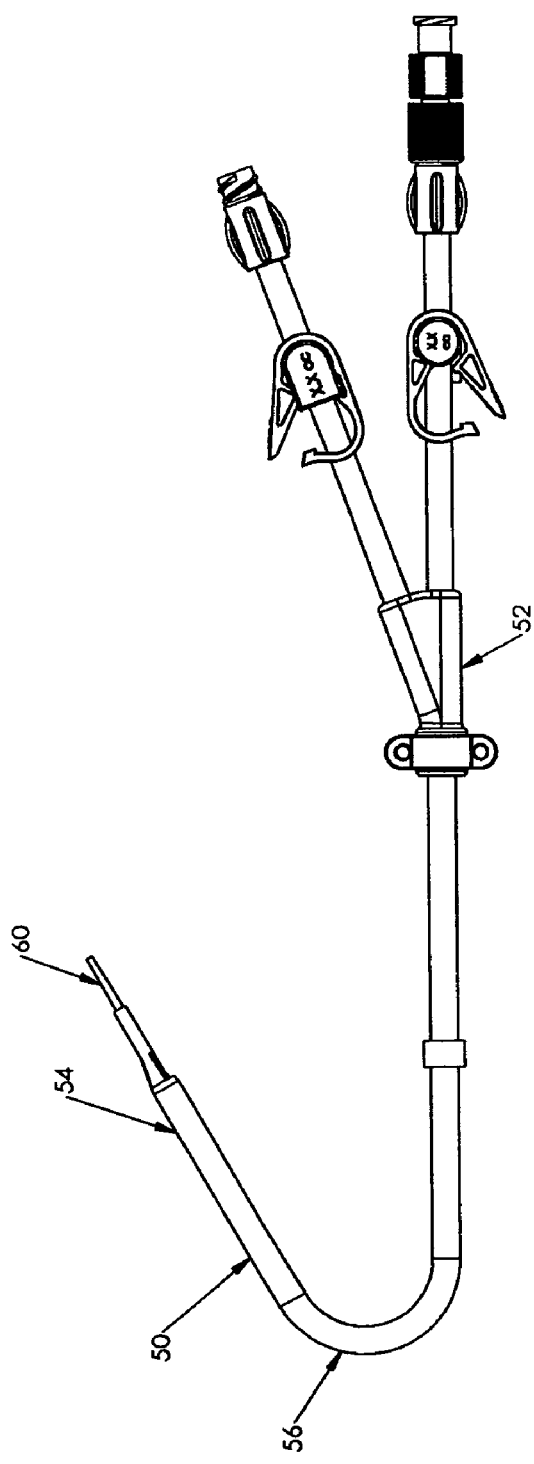
FIG. 2 is a top plan view of a catheter without the aid of the pre-curved catheter clip of FIG. 1.

Referring to FIG. 1, a pre-curved catheter clip 100 according to a first embodiment of the present invention is shown. The pre-curved catheter clip 100 is used to protect, and maintain the curved shape of a pre-curved catheter during sterilization, packaging, and shipping. Typically, a pre-curved catheter 50 having a proximal end 52 and a distal end 54, as shown in FIG. 2, has a curved lumen portion 56 extending between the proximal end 52 and the distal end 54 that is formed during catheter manufacture, with the curved lumen portion 56 having noncurved end portions proximate the curved lumen portion and intermediate and spaced from the distal and proximal catheter ends 54, 52. The catheter 50 is preferably a dual lumen catheter having two lumens, such as side-by-side or co-axial lumens, although those skilled in the art will recognize that the catheter 50 may be a single lumen catheter or a catheter having more than two lumens.

Figure 3:
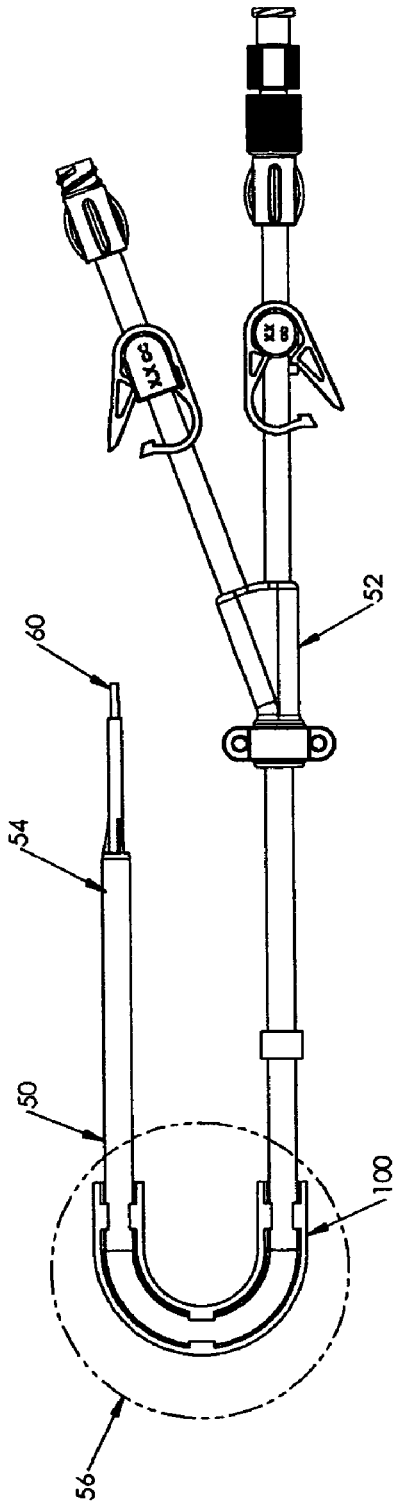
FIG. 3 is a top plan view of the pre-curved catheter clip of FIG. 1, with a catheter disposed therein.

A stylet 60 is inserted through the catheter 50. The stylet 60 provides stiffening support for the catheter 50 during insertion of the catheter 50 into a patient during catheterization of the patient. Ideally, the proximal end 52 and the distal end 54 of the catheter 50 are generally parallel to each other. However, as seen in FIG. 2, the proximal end 52 and the distal end 54 of the catheter 50 are approximately 45 degrees out of parallel. The stylet 60 is straight, and tends to at least partially straighten the catheter 50 after the stylet 60 is inserted thereinto, resulting in the approximate 45 degree angle of the distal end 54 of the catheter with respect to the proximal end 52 of the catheter 50. The catheter clip 100 according to the present invention is used to maintain the proximal end 52 and the distal end 54 of the catheter 50 in a generally parallel relationship during packaging, sterilization, and shipping, as shown in FIG. 3.

Referring back to FIG. 1, the pre-curved catheter clip 100 includes a body 102. The body 102 includes a first straight portion 104 and a second straight portion 106. The first straight portion 104 includes a first open end 108 and a first connection end 110. The first straight portion 104 also includes a first longitudinal axis 111 extending therethrough. The second straight portion 106 includes a second open end 112 and a second connection end 114, and also includes a second longitudinal axis 115 extending therethrough, generally parallel to the first longitudinal axis 111. Preferably, the first and second straight portions 104, 106 are each approximately 1.27 cm (0.50 inches) long, although those skilled in the art will recognize that the first and second straight portions 104, 106 may be longer or shorter than 1.27 cm. A curved connecting portion 116 connects the first and second connection ends 110, 114. Preferably, the connecting portion 116 has a bend radius of approximately 1.60 cm (0.63 inches) in order to maintain curvature of a pre-curved catheter installed in the clip 100, but without kinking the catheter.

Figure 4:
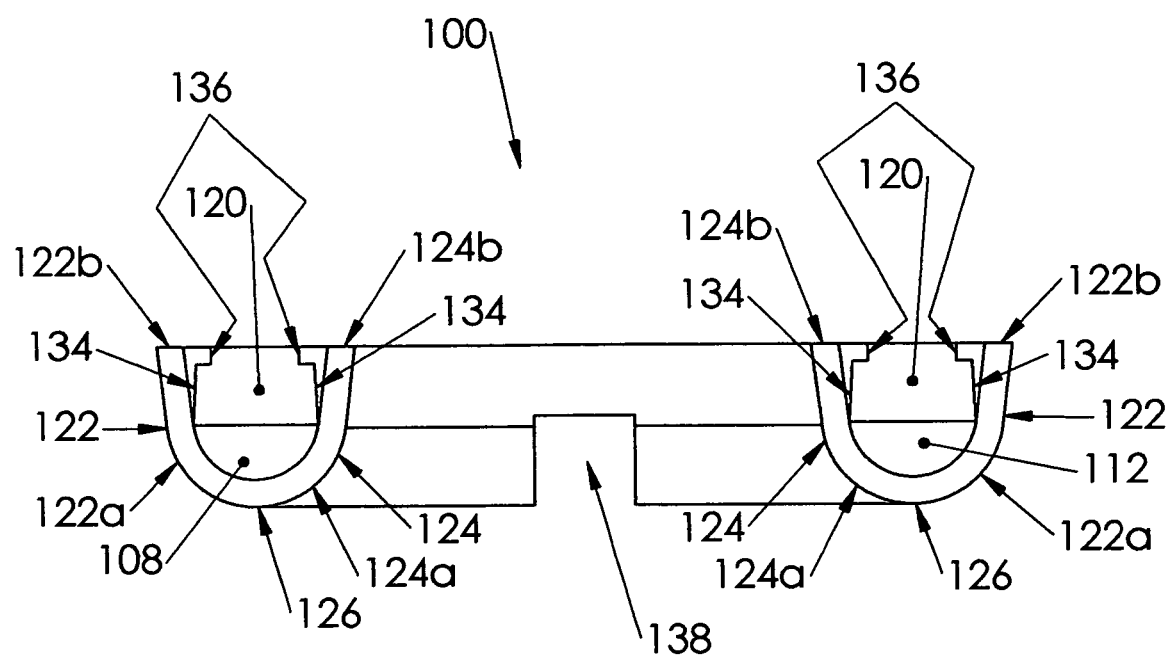
FIG. 4 is a front profile view of the pre-curved catheter clip of FIG. 1.

A channel 120 extends through the body 102 from the first open end 108, through the first straight portion 104, the connecting portion 116 and the second straight portion 106, to the second open end 112. As seen in FIG. 4, the channel 120 is generally "U-shaped" in cross section. The channel 120 includes an outer wall 122 and an inner wall 124. Bottom portions 122a, 124a of each of the outer wall 122 and the inner wall 124 are connected to each other by a generally curved foundation 126.

Figure 5:
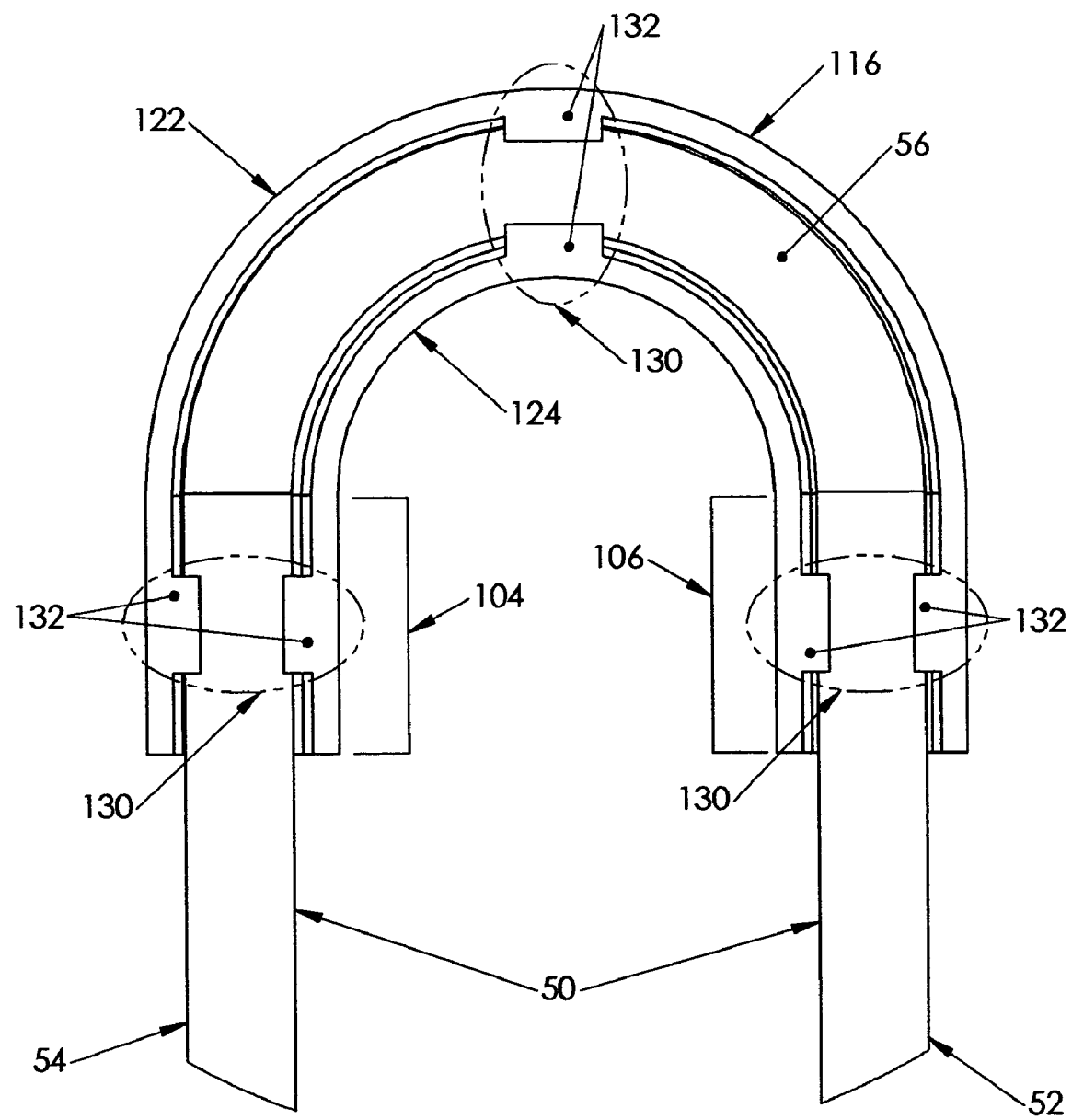
FIG. 5 is an enlarged top plan view of the pre-curved catheter clip of FIG. 3.

At least one retention section is defined on each of the first and second generally straight portions 104, 106 that would fasten directly onto or about the catheter in such a manner requiring the catheter to be forced thereinto from laterally thereof The pre-curved portion of the catheter can be said to define a plane, as is discernable in FIG. 2, and the clip is fastened to the catheter from laterally of that plane. The retention section may be a locking clasp or pair of cooperating locking clasps, or may be a force fit between opposing walls of each of portions 104, 106, or may be a latch arm or the like. Preferably, at least one locking clasp assembly 130 extends from each of the outer wall 122 and the inner wall 124. However, those skilled in the art will recognize that more than one locking clasp assembly 130 may be used as part of the general principle of the invention. FIG. 5 shows three locking clasp assemblies 130, with the first locking clasp assembly 130 on the first straight portion 104, the second locking clasp assembly 130 on the second straight portion 106, and the third locking clasp assembly 130 on the connecting portion 116, as a non-limiting example of the number and locations of locking clasp assemblies 130 mounted on the body 102.

Each locking clasp assembly 130 preferably includes a locking clasp 132 disposed on the outer wall 122 and a locking clasp 132 extending from the inner wall 124. However, those skilled in the art will recognize that each locking clasp assembly 130 may consist of only one locking clasp 132 extending from either the outer wall 122 or the inner wall 124, with a corresponding locking clasp 132 on the inner wall 124 or the outer wall 122 being omitted.

Referring back to FIG. 4, each locking clasp includes a tapered portion 134 that extends upward from bottom portion of its respective outer wall 122 or inner wall 124 into the channel 120. A cantilevered portion 136 extends from the tapered portion 134 into the channel 120. A cutout 138 is formed in the foundation 126 directly below each locking clasp assembly 130. The cutout 138 facilitates insertion and removal of the catheter 50 from the clip 100 by allowing the clip 100 to flex in the proximity of the cutout 138.

Preferably, the channel 120 has a diameter sufficient to accept a catheter of varying sizes, and the locking clasp assembly 130 is able to retain such catheters within the channel 120. Preferably, the clip 100 may be used on catheters varying between 12 and 16 French, although those skilled in the art will recognize that the dimensions of the clip may be modified to accept and retain larger or smaller catheters.

Preferably, the pre-curved catheter clip 100 is constructed from a polymer, such as polypropylene. However, the use of any other polymer or similar material of a life strength and composition is also within extent of the present invention.

To insert the catheter 50 into the clip 100, the lumens of the catheter 50 are forced past each of the locking clasp assemblies 130 and into the channel 120. The cutout 138 proximate to each locking clasp assembly 130 allows the body 102 of the clip 100 to flex sufficiently to allow the catheter 50 to be inserted into the channel 120. Once the catheter 50 is secured within the pre-curved catheter clip 100, the catheter 50 is ready for sterilization and packaging.

When the catheter 50 is ready for use on a patient, the pre-curved catheter clip 100 must be removed from the catheter 50 before insertion. One method of removing the catheter 50 from the pre-curved catheter clip 100 involves forcing the lumens past the cantilevered portion 136 of each locking clasp 132. Once the catheter 50 is fully removed from the locking clasps 132, the catheter 50 is ready for insertion into a patient.

Another method for the removal of the catheter 50 from the clip 100 is to pull the catheter lumens through the channel 120 from the proximal end 52 of the catheter 50. The pulling of the lumens allows the distal end 54 of the catheter 50 to enter into the first open end 108 of the body 102. The distal end 120 of the catheter then passes through the channel 120, underneath of all of the locking clasp assemblies 130 and then exits the channel 120 through the second open end 112. Upon removal of the catheter 50 from the clip 100, the catheter 50 is now ready for insertion into the patient and the clip 100 is discarded.

Figure 6:
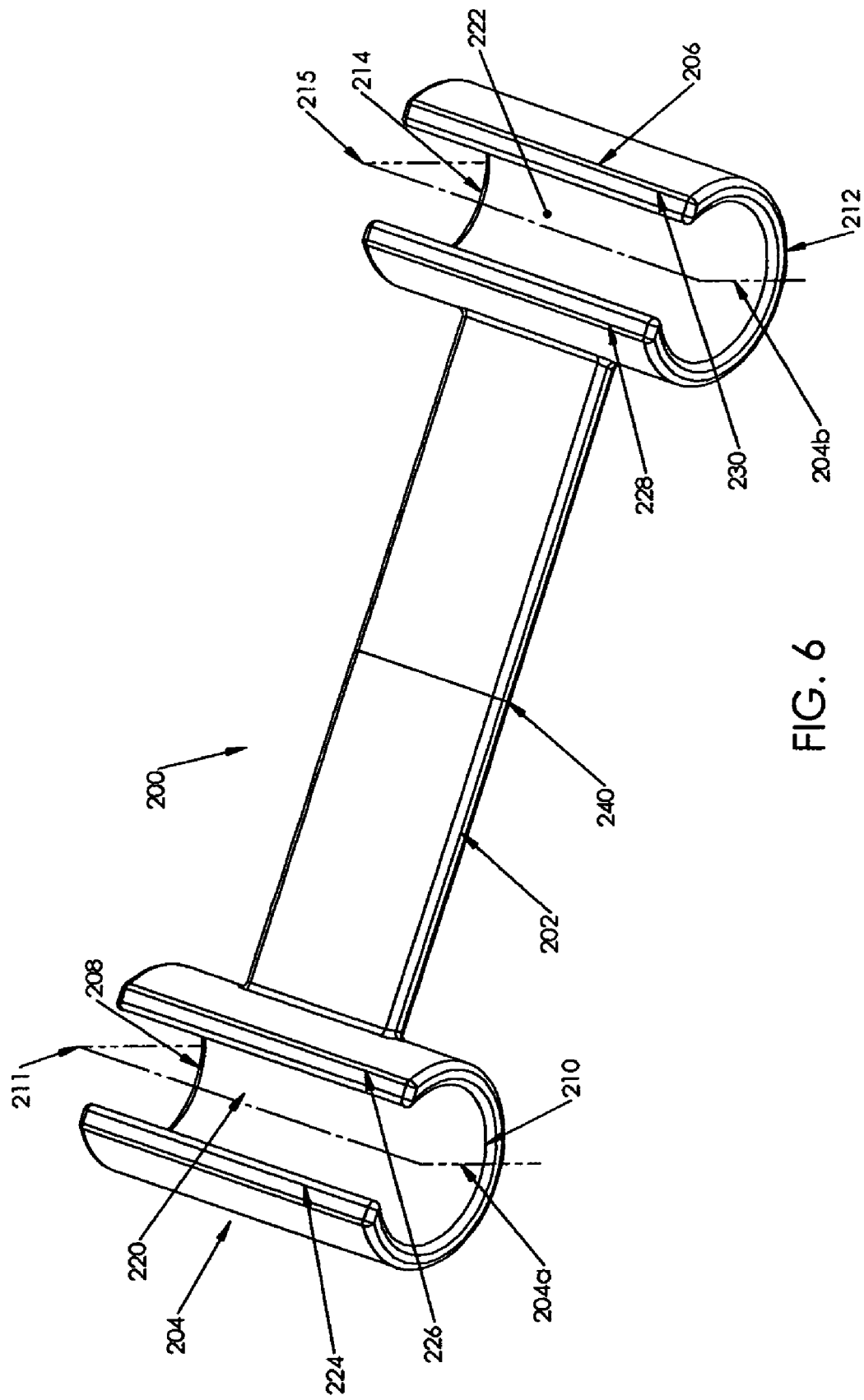
FIG. 6 is a perspective view of a pre-curved catheter clip according to a second preferred embodiment of the present invention.
Figure 7:
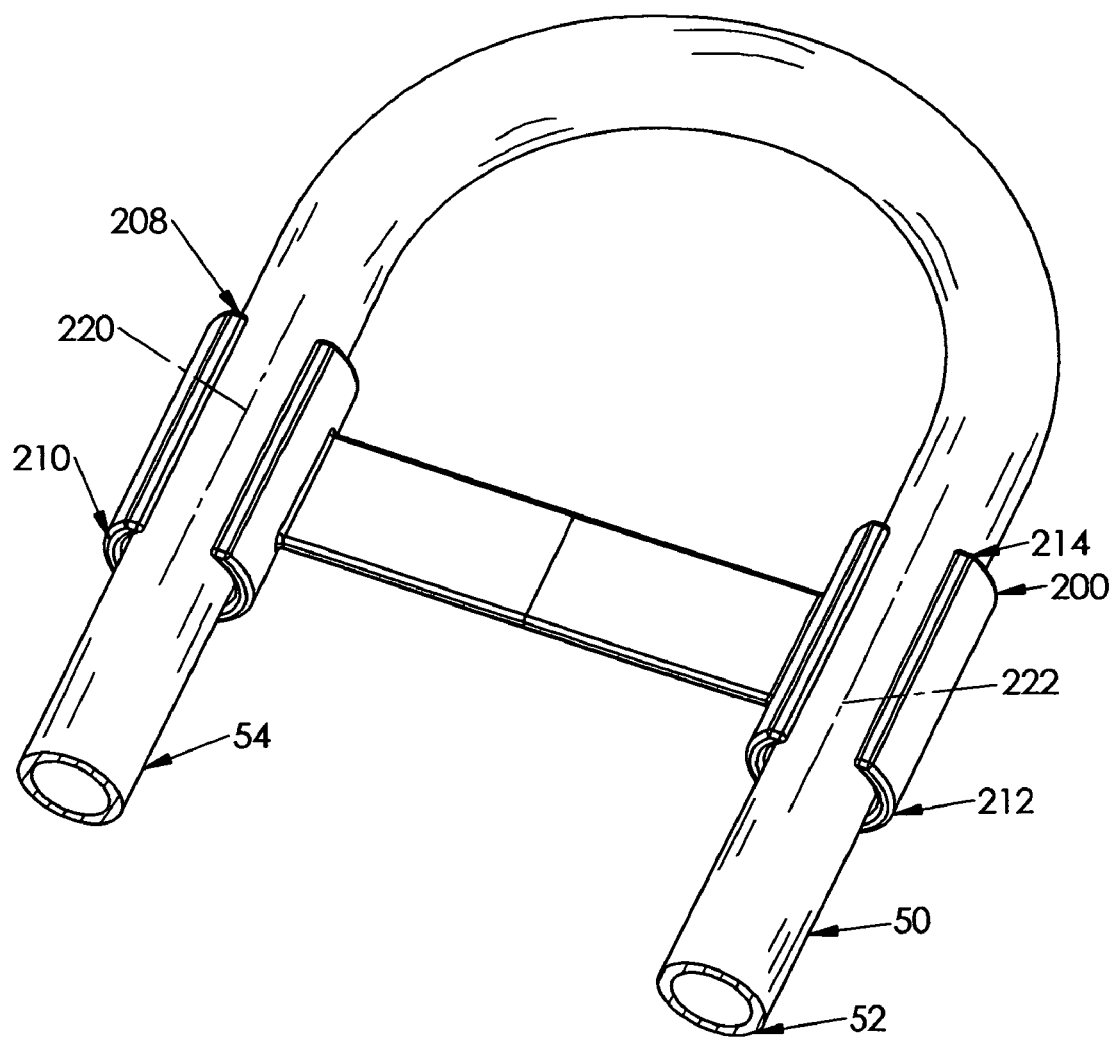
FIG. 7 is a perspective view of the clip of FIG. 6, with a catheter inserted therein.

A second embodiment of a pre-curved catheter clip 200 of the present invention is shown in FIGS. 6 and 7. The clip 200 includes a body 202. The body 202 includes a first generally straight portion 204 and a second generally straight portion 206. The first generally straight portion 204 includes a first proximal end 208 and a first distal end 210. The first generally straight portion 204 also includes a first longitudinal axis 211 extending therethrough. The second generally straight portion 106 includes a second proximal end 212 and a second distal end 214, and also includes a second longitudinal axis 215 extending therethrough, generally parallel to the first longitudinal axis 211. Preferably, the first and second generally straight portions 204, 206 are each approximately 1.27 cm (0.50 inches) long, although those skilled in the art will recognize that the first and second generally straight portions 204, 206 may be longer or shorter than 1.27 cm.

The first generally straight body portion 204 and the second generally straight body portion 215 each have a generally "C-shaped" cross-section. The C-shape of the first generally straight body portion 204 forms a first channel 220. The C-shape of the second generally straight body portion 215 forms a second channel 222. The first generally straight body portion 204 includes two juxtaposed edges 224, 226 across the longitudinal axis 211. The second generally straight body member also includes two juxtaposed edges 228, 230 across the second longitudinal axis 215. The first generally straight body portion 204 acts as a first locking clasp and the second generally straight body portion 206 acts as a second locking clasp. The C-shaped cross-sections retain a catheter within the channels 220, 222. An extension brace 240 connects the first and second generally straight body portions 204, 206 and extends generally perpendicular to the first and second longitudinal axes 211, 215.

Preferably, the channels 220, 222 each have a diameter sufficient to accept a catheter of varying sizes. Preferably, the clip 200 may be used on catheters varying between 12 and 16 French, although those skilled in the art will recognize that the dimensions of the clip may be modified to accept and retain larger or smaller catheters.

Preferably, the pre-curved catheter clip 200 is constructed from a polymer, such as polypropylene. However, the use of any other polymer or similar material of a life strength and composition is also within extent of the present invention.

The catheter 50 described above with respect to the clip 100 may also be used in respect to the second embodiment of the clip 200. To install the catheter 50 into the clip 200, the catheter 50 is pressed against the two juxtaposed edges 224, 226 of the first generally straight body portion 204 and forced into the first channel 220. The catheter 50 is then pressed against the two juxtaposed edges 228, 230 of the second generally straight body portion 206 and forced into the second channel 222. The catheter 50 is now secured within the pre-curved catheter clip 200, as shown in FIG. 7, and the catheter 50 is ready for packaging and sterilization.

The catheter 50 must be removed from the clip 200 before the use of the catheter 50 on a patient. To remove the catheter 50 from the clip 200, the catheter 50 is forced past the two juxtaposed edges 224, 226 of the first generally straight body portion 204 and the catheter 50 is removed from the first channel 220. The catheter is then forced past the two juxtaposed edges 228, 230 of the second generally straight body portion 206 and the catheter 50 is removed from the second channel 222.

Another method of removing the catheter 50 from the clip 200 is to pull the distal end 54 of the catheter 50 from the first distal end 210, through the first distal channel 220, and out the first proximal end 208 of the first generally straight portion 204. Then, the distal end 54 of the catheter 50 is pulled from the second distal end 214, through the second distal channel 222, and out of the second proximal end 212 of the second generally straight portion 206.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A clip for a catheter having a portion having a pre-defined curve with noncurved portions proximate thereto intermediate and spaced from distal and proximal catheter ends, the pre-curved portion defining a plane, comprising:
   a first generally straight body portion having a first generally U-shaped cross section defining a catheter-receiving channel, and a first longitudinal axis extending therethrough;
   a second generally straight body portion having a second generally U-shaped cross section defining a catheter-receiving channel, and a second longitudinal axis extending therethrough, wherein the second longitudinal axis is generally parallel to and offset from the first longitudinal axis;
   a connecting portion connecting the first generally straight body portion and the second generally straight body portion;
   the first and second straight body portions and connecting portions being sized, shaped and relatively positioned to correspond with and to complement the pre-curved catheter portion when the noncurved catheter portion end portions are inserted into the catheter-receiving channels of the first and second generally straight body portions; and
   first and second catheter retention sections defined respectively on the first and second generally straight body portions, are spaced apart from and not continuous with each other and having respective lengths that when added together total less than the longitudinal length of the catheter-receiving channel, each catheter retention section including a narrow entrance portion dimensioned less than a width of the channel, the entrance portions facing in a common direction away from bottoms of the channels to fasten directly onto or about the catheter at respective ones of the noncurved catheter portions in such a manner requiring the catheter to be forced thereinto from laterally thereof, and thereafter assuredly securing the body portion of the clip to the catheter,
   whereby the clip is fastenable to the catheter from laterally of the plane defined by the pre-curved portion of the catheter, at the catheter's pre-curved portion and thereafter maintains the pre-curved shape of the pre-curved catheter portion during shipping and handling.

2. The clip claimed in claim 1, wherein the connecting portion is curved.

3. The clip claimed in claim 2, further comprising a continuous catheter-receiving channel extending through the first generally straight body portion, the connecting portion, and the second generally straight body portion.

4. The clip claimed in claim 3, wherein each catheter retention section comprises at least one locking clasp extending into the channel.

5. The clip as claimed in claim 4 wherein the body comprises an outside wall and an inside wall, and a channel bottom extending between the outside wall and the inside wall that is rounded transverse to the direction of the channel.

6. The clip as claimed in claim 5 wherein the outside wall and the inside wall include beveled interior edges.

7. The clip as claimed in claim 5 wherein the rounded channel bottom includes a cut out disposed proximate to each of the at least one locking clasp, wherein each cut out extends between the outside wall and the inside wall.

8. A method of removal of a catheter from the clip of claim 4 comprising:
   forcing the catheter past each of the at least one retention section while pulling the catheter from the channel.

9. The method of removal of a catheter from the clip claimed in claim 8, further comprising removing the catheter from the clip prior to inserting the catheter into a patient.

10. A method of removal of a catheter from the clip of claim 4 comprising:
    providing a catheter with a proximal end and a distal end and a pre-curved portion therebetween having first and second generally straight portions intermediate and spaced from distal and proximal catheter ends; sliding the catheter out of the clip, by pulling from the proximal end of the catheter relative to the clip so as to allow the distal end to enter the channel of the clip from the first generally straight portion and exit the clip from the second generally straight portion.

11. The method of removal of a catheter from the clip claimed in claim 10 further comprising removing the catheter from the clip prior to inserting the catheter into a patient.

12. A method of use of a clip for a catheter having a pre-defined curved portion as claimed in claim 4 comprising:
   providing a catheter having a distal end and a proximal end and a pre-curved portion therebetween having first and second generally straight portions intermediate and spaced from distal and proximal catheter ends, wherein a clip is placed about the pre-curved catheter portion to maintain the curvature of the pie-curved portion of the catheter within the clip; and
   releasably securing the catheter to the clip by securing the catheter within the at least one retention section on at least the first and second generally straight portions.

13. The clip claimed in claim 2, wherein the first generally straight body portion has a first open end and the second generally straight body portion has a second open end.

14. A method of use of a clip for a catheter having a pre-defined curved portion as claimed in claim 2 comprising:
   providing a catheter having a distal end and a proximal end and a pre-curved portion therebetween having first and second generally straight portions intermediate and spaced from distal and proximal catheter ends, wherein a clip is placed about the pre-curved catheter portion to maintain the curvature of the pre-curved portion of the catheter within the clip; and
   releasably securing the catheter to the clip by securing an associated respective portion of the catheter adjacent to the pre-curved portion of catheter within the at least one retention section on at least the first and second generally straight portions.

15. The clip claimed in claim 1, wherein the clip is comprised of a polymer material.

16. The clip claimed in claim 15, wherein the polymer material is comprised of polypropylene.

17. The clip claimed in claim 1, wherein the first and second catheter retention sections do not project beyond top surfaces of side walls defining the channel.

18. In combination, a clip and a catheter having a pre-curved portion, comprising:
   a catheter having a portion having a pre-defined curve with noncurved portions proximate thereto intermediate and spaced from distal and proximal catheter ends; and
   a clip having:
   a first generally straight body portion having a first generally U-shaped cross section defining a catheter-receiving channel, and a first longitudinal axis extending therethrough;
   a second generally straight body portion having a second generally U-shaped cross section defining a catheter-receiving channel, and a second longitudinal axis extending therethrough, wherein the second longitudinal axis is generally parallel to and offset from the first longitudinal axis;
   a connecting portion connecting the first generally straight body portion and the second generally straight body portion; and
   first and second catheter retention sections defined respectively on the first and second generally straight body portions, are spaced apart from and not continuous with each other and having respective lengths that when added together total less than the longitudinal length of the catheter-receiving channel each including a narrow entrance portion dimensioned less than the catheter diameter, the entrance portions facing in a common direction away from bottoms of the channels to clip onto the catheter end portions when the noncurved catheter portions are inserted thereinto and thus assuredly secure the body portion of the clip to the catheter, which in turn maintains the curvature of the pre-defined curved catheter portion during shipping and handling.

19. The combination of claim 18, further including a stylet extending through the catheter.

20. The clip claimed in claim 18, wherein the first and second catheter retention sections do not project beyond top surfaces of side walls defining the channel.

* * * * *

UNITED STATES PATENT AND TRADEMARK OFFICE
CERTIFICATE OF CORRECTION

PATENT NO. : 7,678,083 B2  Page 1 of 1
APPLICATION NO. : 11/210549
DATED : March 16, 2010
INVENTOR(S) : John Stephens It is certified that error appears in the above-identified patent and that said Letters Patent is hereby corrected as shown below:

Cover page, item 54 and col. 1, line 1, Title: please replace "TIP" with --CLIP--.

Signed and Sealed this

Twentieth Day of April, 2010

David J. Kappos
*Director of the United States Patent and Trademark Office*